United States Patent
McLendon et al.

(10) Patent No.: US 11,887,729 B2
(45) Date of Patent: Jan. 30, 2024

(54) PERSONALIZED EXTENDED DIGITAL MIGRAINE DIARY

(71) Applicant: SensorRX, Inc., Davidson, NC (US)

(72) Inventors: George McLendon, Davidson, NC (US); Alexander Dzeda, Davidson, NC (US); Joshua Phipps, Davidson, NC (US); Elizabeth Shannon Stearman, Davidson, NC (US)

( * ) Notice: Subject to any disclaimer, the term of this patent is extended or adjusted under 35 U.S.C. 154(b) by 636 days.

(21) Appl. No.: 17/107,501

(22) Filed: Nov. 30, 2020

(65) Prior Publication Data

US 2021/0142897 A1    May 13, 2021

Related U.S. Application Data (63) Continuation-in-part of application No. 16/679,231, filed on Nov. 10, 2019, now Pat. No. 10,878,691.

(51) Int. Cl.
    *G16H 50/20*      (2018.01)
    *G16H 50/30*      (2018.01)
    (Continued)

(52) U.S. Cl.
    CPC ........... *G16H 40/67* (2018.01); *A61B 5/4824* (2013.01); *A61B 5/7275* (2013.01);
    (Continued)

(58) Field of Classification Search
CPC ........ A61B 2505/07; A61B 2560/0252; A61B 2560/0257; A61B 2562/029; A61B 5/0022; A61B 5/02055; A61B 5/165; A61B 5/4076; A61B 5/4815; A61B 5/4824; A61B 5/6898; A61B 5/7267; A61B 5/7275; A61B 5/7282; A61B 5/746; A61B 5/4094; A61B 2562/0219; A61B 5/02405; A61B 5/11; A61B 5/389; A61B 5/6803; A61B 18/02; A61B 18/06; A61B 18/1492; A61B 18/18; A61B 18/1815; A61B 18/24; A61B 2018/00434; A61B 2018/00577; A61B 2018/0293; A61B 2018/1861; A61B 2090/365; A61B 2090/374; A61B 2560/0242; A61B 2560/045;
(Continued)

(56) References Cited

U.S. PATENT DOCUMENTS

10,945,604 B2 * 3/2021 Federoff ................ G16H 50/20
2018/0000425 A1 * 1/2018 Hernacki ............... A61B 5/746
(Continued)

*Primary Examiner* — Dionne Pendleton
(74) *Attorney, Agent, or Firm* — John L. Sotomayor (57) ABSTRACT

This document presents a system and method for analyzing migraine related sensor and diary data to permit the prediction of migraine headaches for individuals. A mobile device is adapted to collect and transmit to a server data content from sensors associated with the mobile device and self-reported data content indicative of contemporaneous environmental conditions and individual physical conditions when the individual is suffering from a migraine headache. The server uses the data content to develop predictive metrics indicative of a correlation between the migraine events and the sensor data. The predictive metrics will provide an alert to a designated individual if it is likely the individual will experience a migraine within a future time period.

10 Claims, 6 Drawing Sheets

(51) Int. Cl.
*G16H 40/67* (2018.01)
*G16H 10/60* (2018.01)
*G16H 50/70* (2018.01)
*G16H 10/20* (2018.01)
*G06N 20/00* (2019.01)
*A61B 5/00* (2006.01)
*H04L 67/12* (2022.01)
*G01N 15/06* (2006.01)
*G16H 20/10* (2018.01)

(52) U.S. Cl.
CPC ............ *A61B 5/7282* (2013.01); *A61B 5/746* (2013.01); *G06N 20/00* (2019.01); *G16H 10/20* (2018.01); *G16H 10/60* (2018.01); *G16H 50/20* (2018.01); *G16H 50/30* (2018.01); *G16H 50/70* (2018.01); *H04L 67/12* (2013.01); *A61B 2560/0252* (2013.01); *A61B 2560/0257* (2013.01); *A61B 2562/029* (2013.01); *G01N 15/06* (2013.01); *G16H 20/10* (2018.01)

(58) Field of Classification Search
CPC .......... A61B 2562/0271; A61B 3/0025; A61B 3/0033; A61B 3/0041; A61B 3/113; A61B 3/14; A61B 5/0024; A61B 5/0051; A61B 5/01; A61B 5/02028; A61B 5/021; A61B 5/024; A61B 5/026; A61B 5/0261; A61B 5/0531; A61B 5/0533; A61B 5/08; A61B 5/0816; A61B 5/0823; A61B 5/1032; A61B 5/1075; A61B 5/1079; A61B 5/1103; A61B 5/1104; A61B 5/1117; A61B 5/1118; A61B 5/1128; A61B 5/113; A61B 5/1135; A61B 5/14542; A61B 5/14551; A61B 5/16; A61B 5/163; A61B 5/259; A61B 5/318; A61B 5/361; A61B 5/398; A61B 5/40; A61B 5/4035; A61B 5/4266; A61B 5/4806; A61B 5/4812; A61B 5/486; A61B 5/4884; A61B 5/681; A61B 5/6814; A61B 5/6823; A61B 5/6833; A61B 5/6846; A61B 5/6892; A61B 5/704; A61B 5/721; A61B 5/7221; A61B 5/7264; A61B 5/7278; A61B 5/7405; A61B 5/744; A61B 5/7445; A61B 5/745; A61B 90/37; A61B 8/5223; G06N 20/00; G06N 3/08; G01N 15/06; G16H 10/20; G16H 10/60; G16H 20/10; G16H 40/63; G16H 40/67; G16H 50/20; G16H 50/30; G16H 50/70; G16H 20/70; G16H 50/50; G16H 80/00; H04L 67/12; H04L 67/306; H04L 67/535; H04L 67/55; G08B 21/0446; G08B 21/0453; A61N 1/36014; A61N 1/3956; A61N 7/02; A61F 2007/0075; A61F 7/007; A61M 5/00

See application file for complete search history.

(56) References Cited

U.S. PATENT DOCUMENTS

| | | | |
|---|---|---|---|
| 2023/0148990 A1* | 5/2023 | Oura | A61B 8/0808 600/438 |
| 2023/0240595 A1* | 8/2023 | Tiron | G16H 10/60 600/301 |
| 2023/0343435 A1* | 10/2023 | Wren | G16H 20/40 |

* cited by examiner

PERSONALIZED EXTENDED DIGITAL MIGRAINE DIARY

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

PRIORITY CLAIM

This Non-Provisional application claims under 35 U.S.C. § 120, the benefit of priority as a Continuation-in-Part to the Non-Provisional Application Ser. No. 16/679,231, filed Nov. 10, 2019, and titled "EXTENDED DIGITAL MIGRAINE DIARY" which is hereby incorporated by reference in its entirety.

BACKGROUND

Migraine is a chronic, neurological disease characterized by recurrent moderate to severe headaches often in association with a number of autonomic nervous system symptoms. Migraines affect nearly one billion people worldwide, and are more common in women than men, at 19% and 11% affected, respectively. Examples of symptoms, by way of non-limiting examples, include nausea, vomiting, blurred vision, nasal stuffiness, diarrhea, frequent urination, pallor, sweating, and sensitivity to light, sound, or smell. Current prevention of migraines includes the use of medications, nutritional supplements, lifestyle alterations, and surgery.

It has been estimated that, worldwide, more than 1 billion people suffer from migraine headaches. Although much is known about these maladies, much remains unknown. In the webpaper entitled, "Migraine: Symptoms and causes" ("Mayo Paper"), the Staff of the Mayo Clinic relate what is generally known about migraines, and what, if anything, sufferers may do to mediate, or possibly avoid, their migraine events. In particular, the Mayo Paper discusses, briefly, a number of known or suspected triggers.

In the past, various peer-reviewed clinical studies have attempted to develop sufficient anecdotal records of actual migraine events to facilitate confirmation of specific event triggers. In these studies, the quality of the data tended to be less than ideal because information relating to each event was based on after-the-event recollections of the sufferers. More recently, attempts have been made to facilitate capture, in near real-time, of migraine related information direct from the sufferers. However, to be most useful in the search for environmentally-based triggers, contemporaneous information must also be collected with respect to those environmental conditions posited to comprise triggers or, perhaps, just trigger factors.

BRIEF DESCRIPTION OF THE DRAWINGS

Certain illustrative embodiments illustrating organization and method of operation, together with objects and advantages may be best understood by reference to the detailed description that follows taken in conjunction with the accompanying drawings in which.

DETAILED DESCRIPTION

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The term "sensor pad" refers to a device that, when engaged by the subject, communicates with the activator. In an embodiment, the sensor pad is a button, dial, switch, touch screen, or microphone. In an embodiment, a button is engaged by pressing on the button. In an embodiment, a dial is engaged by turning the dial. In an embodiment, the switch is engaged by pressing or toggling the switch. In an embodiment, a touch screen is a surface utilizing a touch detection technology. In an embodiment, the touch detection technology includes resistive, capacitive, infrared, surface acoustic wave, and near field imaging technologies.

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker).

"Treating" or "treatment" of a state, disorder or condition (e.g., migraine) includes: (1) preventing or delaying the appearance of clinical or sub-clinical symptoms of the disorder developing in a human that is afflicted with or pre-disposed to the disorder but does not yet experience or display clinical or subclinical symptoms of the disorder; and/or (2) inhibiting the disorder, including arresting, reducing or delaying the clinical manifestation of the disorder or at least one clinical or sub-clinical symptom thereof; and/or (3) relieving the disorder, e.g., causing regression of the disorder or at least one of its clinical or sub-clinical symptoms; and/or (4) causing a decrease in the severity of one or more symptoms of the disorder. The benefit to a subject to be treated is either statistically significant or at least perceptible to the patient or to the physician.

Migraines are often triggered by environmental cues, such as changes in the weather, light, sound, air quality, and odors. Avoidance of these triggers, in addition to acute symptomatic control and pharmacological prevention, helps to manage migraines. Monitoring exposure to potential triggers can help an individual pinpoint triggers likely to contribute to development of a migraine.

Having once collected a sufficiently large set of reliable event records, together with contemporaneous environmental condition data, known numerical analysis techniques, such as regression analysis, can be employed to determine if a statistically significant correlation exists between the recorded events and the recorded environmental conditions. As is known, a statistically significant correlation is indicated by a probability value of less than 0.05, i.e., that the probability of obtaining such a correlation coefficient by chance is less than five times out of 100, so the result indicates the presence of a relationship.

Having finally detected a probable trigger, the problem remains, however, of how to make practical use of this information better to predict future migraine events on a sufferer-by-sufferer basis. We submit that what is needed is a migraine prediction method that is more efficient and effective than the known art.

In an embodiment, the system herein described may provide a real-time diagnosis of migraines for patients who have used a distributed data collection migraine diary process for a significant amount of time. The migraine dairy application may import healthkit data (direct/indirect measurements using wearables as well as self-reported), as well as data collected from sensors that may be incorporated into the healthkit. Such sensors may collect and store data regarding migraine intensity, sound, pressure, temperature, and humidity that exist at the time a patient indicates a migraine event. Additionally, stress measurements are also able to be made and incorporated using heart rate sensors that are attached to the patient.

In an embodiment, a key to prediction is that in most cases a single trigger may not result in an episode whereas more than one trigger can push beyond the threshold to trigger a migraine episode. In this regard, necessary self-reports are supported by independent variables like weather, exercise, sleep data and other self-reported data such as start and stop time for monthly menstruation cycles. Weather data may be derived from GPS and NOAA data, where exercise and sleep data may be derived from healthkit data.

Often times, patients think that their migraines are entirely brought on by weather (to the point that some of our users have moved for supposed better weather areas), or entirely by eating an onion, etc. While these may be contributing factors, other information can take this from a hunch to an actual trigger that can be described as a set of parameters/conditions conducive for a migraine. In a non-limiting example, there is a widespread myth that barometric pressure has a direct correlation to headache onset, and then people get anxious and stress themselves into having a migraine when they see the pressure is dropping.

In an embodiment, the system is active to provide a real-time diagnosis of migraine episodes for each patient or user who has utilized the application available to the user over a significant span of time, where a significant span of time may be defined as a span of time over which the patient or user has experienced and recorded a statistically significant number of migraine events for that user or patient. The system is active to generate daily and hourly migraine forecast messages for each patient and/or user through the utilization of neural network models to analyze gathered migraine episode information.

In an embodiment, for each patient or user an optimal neural network architecture and the weighting of data parameters may be found through analysis and information update of patient historical data combined with cross validation testing. In a non-limiting example, the neural network accepts for each patient or user observed input parameters including collected weather data, menstrual cycles, and collected health data, as well as weather data from a patient or user's recorded location, such as humidity, barometric pressure, temperature, wind speed, and other weather information. Menstrual cycle data is collected by a patient entering the start and end times of the current cycle for each individual for whom this data is relevant. This information is transformed into a binary variable for does/does not have period.

In an embodiment, as data is collected from patients or users, all collected information is appended to one or more training and/or historical data sets to establish a migraine/no migraine threshold value for the patient or user. The addition of the collected information permits the system to retrain and improve the models toward improving predictions made for the individual based upon the values for the collected data that determined the threshold for the value of "migraine" for that individual patient or user. The collection of all current observed and reported input variables supports a real-time diagnosis of an impending migraine episode for an individual patient or user as measured against the historical threshold value of a migraine episode occurring for that individual patient or user. All collected data is provided to the one or more prediction models and the calculation is performed to create an output variable classification for the diagnosis as a migraine occurrence value. This output variable classification is compared against the individual migraine occurrence threshold value for the patient or user and provides a value for the probability of the patient or user experiencing a migraine within a requested time frame. The migraine probability for the patient or user is transmitted to the patient or user as a prediction alert along with the time frame for which the prediction alert is valid.

In an embodiment, for each patient, the optimal neural network architecture and weight parameters used in creating a prediction metric expressed as the migraine probability value may be at least partially found through analysis of a patient's historical data and cross validation testing to learn the particular triggers that may be associated with the onset of a migraine for a particular individual. The prediction metric may be composed of particular triggers associated with a particular individual and the prediction metric applied to collected environmental, physiological, and historic data to create a prediction alert and a recommended course of action to reduce or eliminate an impending migraine headache for the individual.

In an embodiment, the migraine associated data collected contemporaneously with a reported migraine episode from an individual may comprise environmental data. In an embodiment, the environmental data is selected from the group consisting of: light, sound, temperature, air quality, humidity, barometric pressure, altitude, location data, or any combination thereof. In an embodiment, the migraine associated data comprises physiological data. In an embodiment the physiological data is selected from the group consisting of: heart, activity, sleep data, oxygen saturation of the blood, and electrodermal activity or any combination thereof. In an embodiment, the migraine associated data comprises self-reported data. In an embodiment the self-reported data is selected from the group consisting of diet, medication, vitamins, supplements, menstruation status, emotional state, pain intensity, migraine location, sleep, activity, biomarker, water intake, or any combination thereof. In an embodiment, the migraine associated data is recorded when the sensor is triggered automatically.

In an embodiment, the measurement of migraine associated data is taken when a sensor is triggered manually. In an embodiment, the migraine associated data is taken as a baseline measurement. A sensor may be associated with a mobile device belonging to a particular individual. A sensor may be a pressure sensor, light sensor, audio sensor, touch sensor, or any other sensor that may be triggered manually by an individual, or that may be triggered automatically by changes in the environment surrounding the individual and the mobile device associated with the individual. Sensors may be incorporated into the mobile device, or may be associated with the mobile device through wired or wireless connections to the mobile device where each sensor is in data communication with the mobile device and the sensor data is captured by the mobile device. In an embodiment, the migraine associated data is taken instantaneously when the sensor is triggered. Thus, sensor data may be collected from sensors comprising a pressure sensor, light sensor, audio sensor, touch sensor, or any other sensor that may be triggered manually by an individual, or that may be triggered automatically by changes in the environment surrounding the individual.

In an embodiment, the measure of migraine associated data may be taken over a period of time after the sensor is triggered. In an embodiment, the baseline measure of migraine associated data may be recorded one, two, three, four, five, six, seven, eight, nine, ten, twelve, twenty four, or forty eight times per day, although these collection timing should in no way be considered limiting as any consistent timing schedule for collecting and recording migraine associated data may be followed by each patient. In an embodiment, the baseline measurement of the migraine associated data is recorded at an interval specified by the individual patient.

In an embodiment, light data comprises a wavelength of light experienced by the individual. In an embodiment, the wavelength of light is on the visible spectrum of light (450 nm-750 nm). In other embodiments, the wavelength of light is not on the visible spectrum of light (e.g. UV light: 100 nm-400 nm). In an embodiment, light data comprises an illuminance of light experienced by the individual where the light, or luminous, intensity is above a pre-configured level, such as, in a non-limiting example, above 7 lux. Light intensity varies with the time of year, time of day, and location of the individual, which requires that light intensity values be regularly sampled and recorded every few minutes, or even more frequently based upon a user's sensitivity to light levels as a migraine trigger. The system may activate a light sensor in a mobile device associated with the user on a relatively regular schedule to capture the light intensity being experienced by the user at the time of each collected measurement. The mobile device may, in a non-limiting example, capture and store a light intensity measurement once each minute, or any other configured time limit between measurements, so that relative changes in ambient light intensity may be identified and reported to the system on a timely basis.

In an embodiment, the system may analyze the user's particular "light intensity" correlation with regard to each captured light intensity measurement to formulate a migraine prediction score. If the migraine prediction score is above a pre-configured threshold level, the system may activate any one or more of a selected set of proactive responses to reduce or otherwise affect the possibility of a user experiencing a migraine. In a non-limiting example, the system may be active to reduce the intensity of the ambient light in the user's location, change the hue of a screen display, transmit a command to a room control facility to close window shades, or perform other actions that result in reducing the experienced light intensity in the user's location.

In an embodiment, sound data comprises a frequency of sound experienced by the individual. In an embodiment, sound data comprises an intensity of sound experienced by the individual.

In an embodiment, temperature data comprises an ambient temperature experienced by the individual. In an embodiment, the ambient temperature ranges from 68° F. to 77° F. (20° C. to 25° C.). In an embodiment, temperature data comprises an outside temperature. In an embodiment, the outside temperature is obtained from an external source, for example from the internet.

In an embodiment, air quality data comprises a level of a contaminant in the air. Examples of air contaminants, by way of non-limiting examples, include ozone, nitrogen dioxide, carbon monoxide, particulate matter ($PM_{10}$ and $PM_{2.5}$), sulphur dioxide, and hydrogen sulphide. In an embodiment, the air quality data is obtained from an external source, for example from the internet.

In an embodiment, humidity data comprises a humidity experienced by the individual.

In an embodiment, barometric pressure data comprises a barometric pressure experienced by the individual. In an embodiment, the barometric pressure data comprises whether the barometric pressure is rising or falling. In an embodiment, the barometric pressure data is obtained from an external source, for example the internet.

In an embodiment, altitude data comprises an altitude of the individual.

In an embodiment, location data comprises a location of the individual. In an embodiment, the location comprises GPS coordinates of the location. In other embodiments, the location comprises a zip code, street, city, or combination thereof. In an embodiment, the location comprises whether the individual is at home, at work, or another location.

In an embodiment, heart data comprises a heart rate of the individual. In an embodiment heart data is an electrocardiogram (ECG) of an individual. In an embodiment, heart data comprises whether the individual has an arrhythmia. In an embodiment, heart data comprises heart rate variability.

In an embodiment, activity data comprises a movement. In an embodiment, the movement is the distance an individual has moved during a day. In an embodiment the distance moved is determined for different periods of the time. Examples of periods of time, by way of non-limiting examples, include general (e.g. morning, afternoon, evening, night) and every hour (e.g. 8-9 am, 9-10 am, and so forth). In an embodiment, the movement is a number of steps an individual has taken during the day or during a period of time. In an embodiment, activity data comprises self-reported data regarding an activity in which the individual has participated. In an embodiment, self-reported activity data further comprises the length of time spent participating in the activity. In an embodiment, the activity is chosen by the individual from a list. Example of activities, by way of non-limiting examples, include archery, badminton, baseball, basketball, biking, bowling, canoeing, cricket, cross-country skiing, curling, fencing, football, golf, gymnastics, hiking, hockey, horseback riding, kayaking, martial arts, rollerblading, rowing, running, skating, skiing, snowboarding, snowshoeing, soccer, swimming, tennis, volleyball, weightlifting, and wrestling. In an embodiment, the individual can manually add an activity to the list.

In an embodiment, sleep data comprises an amount of sleep an individual has experienced. In an embodiment, the amount of sleep is automatically recorded or is self-reported. In an embodiment, sleep data comprises a quality of sleep for the individual. In an embodiment, quality of sleep is automatically recorded. In an embodiment, the quality of sleep comprises the amount of movement during sleep. In an embodiment, the quality of sleep comprises the amount of time spent in each stage of sleep. In an embodiment, the quality of sleep comprises the stage of sleep during which an individual awakens. In an embodiment, the quality of sleep is self-reported. In an embodiment, self-reported quality of sleep data comprises a scale of the quality of sleep the individual feels they experienced. A non-limiting example of a scale of quality of sleep is scale of 1 to 5, wherein 1 is a very restful sleep and 5 is a very unrestful sleep. In an embodiment, self-reported quality of sleep data comprises illustrations of facial expressions wherein the facial expressions are representative of the quality of sleep an individual feels they experienced.

In an embodiment, oxygen saturation of the blood comprises an oxygen level of the blood.

In an embodiment, electrodermal activity comprises a measure of galvanic skin response.

In an embodiment, dietary data comprises whether an individual consumed a meal (e.g. breakfast, lunch, dinner) or a snack. In an embodiment, the dietary data comprises a time the meal or snack was consumed. In an embodiment, the dietary data comprises a type of food or beverage consumed. In an embodiment, the dietary data comprises a time a food or beverage was consumed. In an embodiment, the dietary data comprises an amount of the food or beverage consumed. In an embodiment, the type of food or beverage consumed chosen by the individual from a list. Examples of types of food and beverages in the list, by way of non-limiting examples, include chocolate, alcoholic beverages (e.g. red wine, white wine, beer, liquor), caffeine containing beverages (e.g. coffee, soda, tea), avocados, beans (e.g. string, navy, kidney, lima), pickled food (e.g. cucumbers, eggs, beets, olives, peppers), bananas, bread, cheese (e.g. cheddar, blue, Brie, aged cheese), chili pepper, pork, soy-based foods, processed meat (e.g. bacon, hot dogs, deli meats, pepperoni, sausage, jerky), nuts, citrus fruits, dried fruits (e.g. prunes, figs, apricots), vinegar (e.g. red vinegar, balsamic vinegar), apples, pears, plums, apple juice, cider, sour cream, milk, and sweeteners (e.g. aspartame). In an embodiment, the individual can manually add a food or beverage item to the list.

In an embodiment, supplement data comprises whether an individual is currently taking a supplement. In an embodiment, the supplement data further comprises a time of day the supplement is taken. In an embodiment, the supplement data further comprises an amount of the supplement taken. In an embodiment, the supplement data is a type of supplement taken. In an embodiment, the type of supplement taken is chosen by the individual from a list. Examples of supplements in the list, by way of non-limiting examples, include vitamin D, vitamin E, vitamin A, vitamin B2, vitamin B3, vitamin B6, vitamin B12, and magnesium, melatonin, butterbur, feverfew, and coenzyme Q10. In an embodiment, the individual can manually add a supplement to the list.

In an embodiment, emotional state data comprises the emotional state of an individual. In an embodiment, the emotional state is chosen by the individual from a list. Examples of emotional states in the list, by way of non-limiting examples, include happy, excited, angry, depressed, anxious, confused, and stressed. In an embodiment, the individual can manually add an emotional state to the list. In an embodiment, the emotional state comprises illustrations of facial expressions representing the emotional state.

In an embodiment, pain data comprises the level of pain of a migraine. In an embodiment, the level of pain of a migraine comprises a scale. A non-limiting example of a scale of pain intensity is scale of 1 to 5, wherein 1 is no pain and 5 is severe, debilitating pain. In other embodiments, the level of pain of a migraine data comprises illustrations of facial expressions wherein the facial expressions are representative of the level of pain an individual is feeling.

In an embodiment, location of a migraine data comprises the area of the body where an individual feels migraine pain. In an embodiment, the location of the migraine data comprises an illustration of a body with various regions highlighted where migraine pain can be experienced wherein the individuals selects the illustration best representing where pain is being experienced. In other embodiments, the location of the migraine data comprises an illustration of a body showing a plurality of points where migraine pain can be experienced wherein the individual selects the points where pain is being experienced. In other embodiments, the location of the migraine comprises an illustration of a body showing a plurality of regions where migraine pain can be experienced wherein the individual selects the regions where pain is being experienced.

In an embodiment, biomarker data comprises genetic, proteinic, hormonic, or other biological data. In an embodiment, genetic data comprises the presence of a single nucleotide polymorphism (SNP), insertion, deletion, inversion, microsatellite, or copy number variant. Examples of SNPs associated with migraines include, but are not limited to, rs1835740, rs1043994, rs1042838, rs2651899, rs10166942, and rs11172113. In an embodiment, proteinic data comprises the presence or quantity of a protein biomarker. Non-limiting examples of protein biomarkers include, but are not limited to: C-reactive protein (CRP), calcitonin gene-related protein (cGRP), or adipokines (e.g. adiponectin). In an embodiment, the hormonic data comprises the presence or quantity of a hormone. Examples of hormones include, by way of non-limiting examples, testosterone, progesterone, and estrogen. In an embodiment, the other biological data comprises the level in the individual of a non-protein biomarker. Examples of non-protein biomarkers include, but are not limited to, vitamin D, blood glucose, lipids (e.g. ceramides), insulin, or homocysteine. In an embodiment, the biomarker is determined from a bodily fluid sample from the individual, such as from the blood, saliva, urine, or stool. In an embodiment, the individual reports biomarker data from a family member.

In an embodiment, the system and method can be described as for each individual in the creation of a prediction metric that is relevant for each individual, finding the optimal combination of connected nonlinear functions that may transform observed input parameters as herein described utilizing the prediction metric as applied to the collected gathered information, both gathered from sensor data and self-reported information, into a binary output target variable. The target variable is the binary outcome of has migraine/no migraine. The observed input parameters include collected weather data, menstrual cycles, self-reported migraine diary entries, and collected health data. The system may collect the weather data using a patient's recorded location, and use the humidity, barometric pressure, temperature, and wind speed readings (among others) at the patient's location to pass into the algorithms. In a non-limiting example, menstrual cycle data is collected by a patient entering their start and end times of the menstrual cycle into the migraine diary. The system transforms all collected menstrual cycle data into a binary variable (does have period/does not have period). The menstruation status data further comprises the current day of the individual's menstrual cycle, wherein day 1 is the day menstruation began.

In an embodiment, as the system collects the data from the patients, the newly collected information is appended to the existing data in the training/historical dataset, which allows the system to retrain and improve the predictive models and the individual prediction metric values. To make a real-time diagnosis, the system collects all the current observed input variables, creates the prediction metric that is associated with each individual, and passes this data to the predictive models to run the calculation of the output variable classification. This classification shows the probability of the individual having a migraine in the requested time frame.

Figure 1:
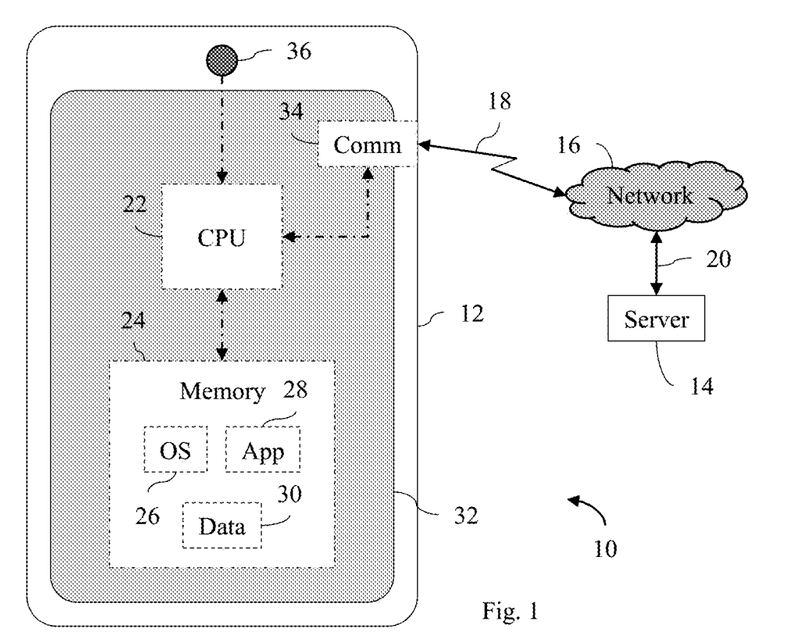
FIG. 1 is a view of a system configured to collect environment and self-reported data during migraine events consistent with certain embodiments of the present invention.

Turning now to FIG. 1, this figure presents a view of a system configured to collect environment and self-reported data during migraine events consistent with certain embodiments of the present invention. In an exemplary embodiment, the migraine analysis system 10 may utilize a mobile device 12, where the mobile device 12 may consist of any device having a data processor that may establish network communication and two-way data communication with a server 14 exterior to the mobile device 12. Thus, by way of illustration and not limitation, the mobile device 12 may be a portable computer, laptop, smart phone, smart watch, tablet, iPad, or any other mobile device. The mobile device 12 and the server 14 are connected through a network cloud 16 where data may be communicated to the cloud 18 and the cloud may then transfer all communications 20 from the mobile device to the server 14. The mobile device 12 may comprise a central processing unit (CPU) 22 that is active to operate the collection of data from the mobile device 12. The mobile device 12 may also comprise an internal electronic memory 24 having the capacity to store and activate an operating system 26, provide storage and operational memory space for the migraine diary data collection application 28, and provide storage for all data captured by the mobile device 12 during operation. A display 32 permits a user to view the data being collected by the mobile device 12 and communicated from the mobile device 12 to the network cloud 16. The mobile device 12 may also be activated by a touch position 36 accessible to a user of the device.

Figure 2:
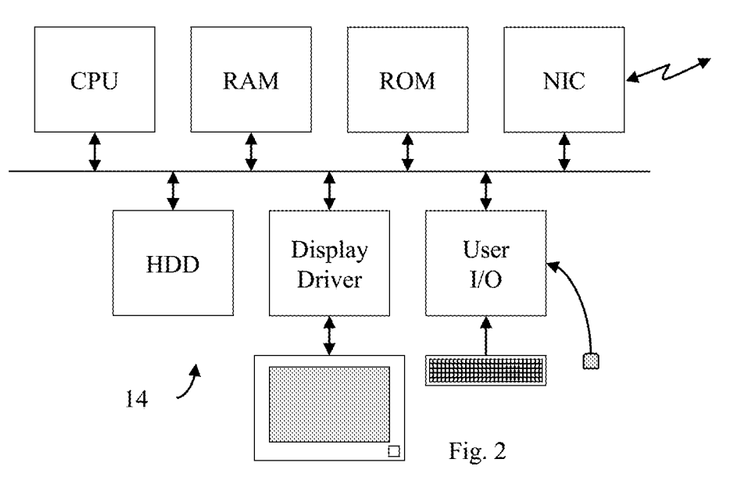
FIG. 2 is a view of a communication capability for the system consistent with certain embodiments of the present invention.

Turning now to FIG. 2, this figure presents a view of a communication bus providing data communication capability for the system consistent with certain embodiments of the present invention. In an exemplary embodiment, the system presents a data communication bus within the server 14 that is active to collect the incoming data communication from a mobile device and provide access to that data both to the analytic and predictive software processes operational within said server 14 and to an individual accessing the server 14.

Figure 3A:
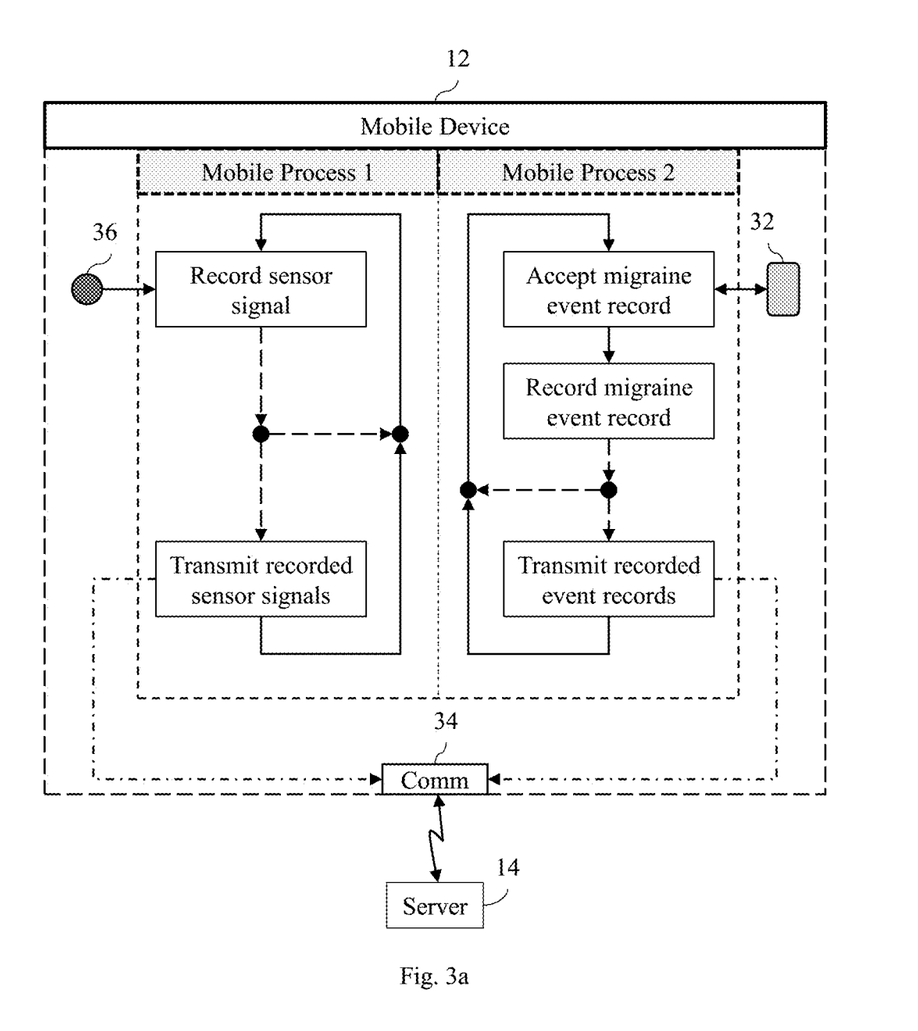
FIG. 3*a* is a view of the flow of data content within a mobile device configured for data collection consistent with certain embodiments of the present invention.

Turning now to FIG. 3a, this figure presents a view of the flow of data content within a mobile device configured for data collection consistent with certain embodiments of the present invention. In an exemplary embodiment, a first process may be active within the mobile device 12 to permit the activation and data collection from one or more sensors that are associated with said mobile device 12. A second process may be active within the mobile device 12 to permit the capture of migraine event records and the transmission of the captured migraine event records to a system server 14 through an established communication channel 34 active within the mobile device 12.

The first and second processes may be activated by a user through the selection of an activation touch position 36 located on the mobile device 12. Once activated, the first process is active to collect sensor signals and record the information from the sensor signals to an electronic storage element within the mobile device 12. The collected and stored sensor signals may then be transferred from the electronic storage element of the mobile device 12 to a system server 14 through an established communication channel 34 active within the mobile device 12. Utilizing the collection and storage capabilities of the first and second processes, the mobile device 12 permits a patient to capture migraine event information actively while the mobile device automatically captures sensor information that is relevant to the time that the migraine event occurred. The migraine sensor information and event records input by a user are combined at the system server 14 to create an entry into a migraine diary maintained by the system server and associated with the user.

Figure 3B:
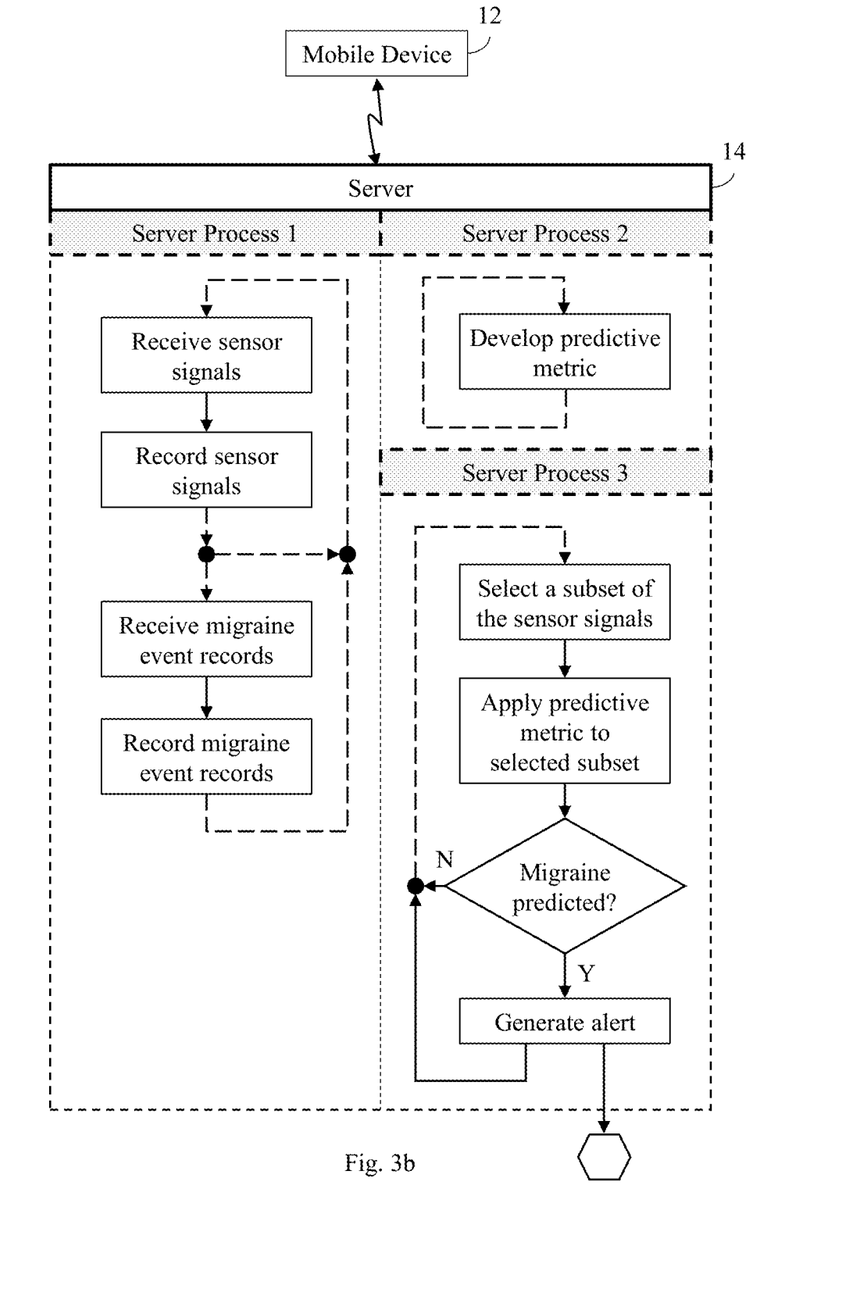
FIG. 3*b* is a view of the process flow of data analysis within a server in communication with a mobile device consistent with certain embodiments of the present invention.

Turning now to FIG. 3b, this figure presents a view of the process flow of data analysis within a system server in communication with a mobile device consistent with certain embodiments of the present invention. In an exemplary embodiment, a mobile device 12 transmits all collected sensor data and user input records to the system server 14 at the time of the occurrence of a migraine event for the user.

Upon receipt of a data communication containing a sensor signal data record from the mobile device, the system server may record the sensor signal data record in an electronic storage device and interrogate the mobile device 12 through the communication channel as to whether additional sensor signals are to be transmitted from the mobile device 12. If additional sensor signals containing sensor data records are received the system server stores those received data records in the electronic storage device. The interrogation and storage of received sensor signal data records continues until all sensor signal data records for a particular migraine event are received by the system server and stored in the record created in the electronic storage device. The system server may also receive migraine event data records from the mobile device 12 and store the received migraine event data records in the record created in the electronic storage device for the particular time and particular user, combining the migraine event data records with the sensor signal data records and collected environmental data readings to create a complete migraine diary record event for a particular event and particular user.

The system server may also initiate a process to develop a predictive metric for each individual based upon the migraine diary data record entries for each user. To develop a predictive metric for the condition of migraine/no migraine, the system server process utilizes input parameters that exist at the day and time that a user indicates a migraine event and includes collected weather data, menstrual cycles, and collected health data where the predictive metric includes the personalized reactions of an individual to all environmental and health conditions to produce a predictive metric that creates an indication of how these environmental and health conditions affect the individual to contribute to a migraine episode, or contribute to the severity of a migraine once it occurs. The system server collects weather data using a patient's recorded location, collecting the humidity, barometric pressure, temperature, wind speed readings, pollen counts, air pollution and particulate matter readings, and other environmental conditions (among others) at the patient's location and storing these readings in the electronic storage data record. These readings may then be combined with the sensor data record and user migraine event data records. The combined data records in combination with the created prediction metric may then be utilized by migraine detection algorithms active in the system server to create a tentative prediction for each individual.

Additional data records such as menstrual cycle information is collected for female patients. The menstrual cycle data is collected by a patient entering their start and end times of the menstrual cycle. The system server process transforms this information into a binary variable (does have period/does not have period). This information is appended to the migraine diary record to optimize the predictive metric for users for whom this information applies.

In a third process in the system server, to make a real-time prediction of a migraine episode occurrence for a particular user, the system server collects all the current observed input variables for a user and passes this data into the predictive models. To determine the predictive metric for a particular individual, the system server selects a subset of the sensor signal data records and user input data records and utilizes this subset to run the calculation of the output variable classification for a migraine episode, and/or the severity of a migraine episode, as a predictive metric. This predictive metric is used to analyze the collected data by the predictive model to indicate the probability of the user having a migraine in a requested time frame. If the result of the predictive model for a particular user indicates that the user may experience a migraine in a near future timeframe. The system server may formulate a migraine prediction alert message and transmit that message, along with a recommended course of action to the affected user to prevent the migraine or reduce the severity of the migraine in a migraine episode.

As data is collected from the patients, all updated and new data is appended to the training/historical migraine diary dataset for all monitored individuals. The training/historical migraine diary dataset, which encompasses all current and historical records for all users, permits the system server process to retrain and improve the migraine predictive models.

Figure 4:
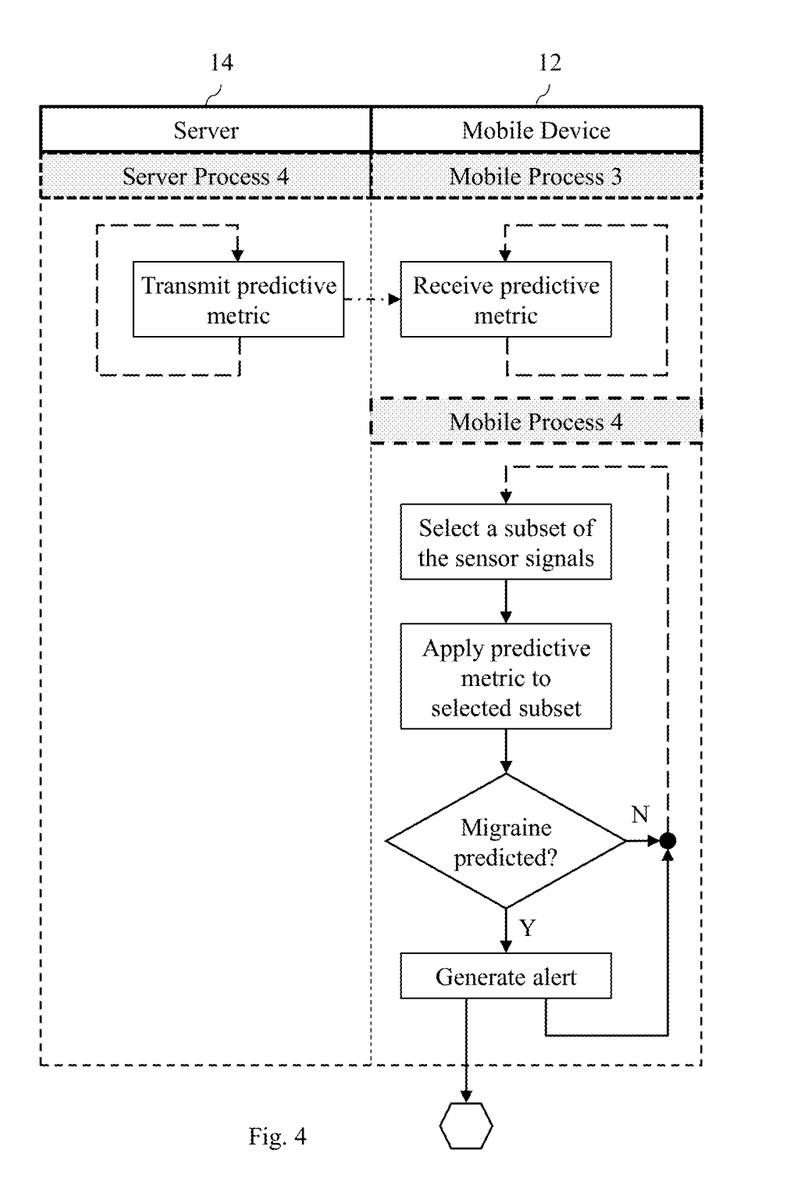
FIG. 4 is a view of the process flow for the creation of an alert for transmission to an individual consistent with certain embodiments of the present invention.

Turning now to FIG. 4, this figure presents a view of the process flow for the creation of a migraine prediction metric for transmission to an individual and transmitting the alert to the mobile device associated with an individual consistent with certain embodiments of the present invention. In an exemplary embodiment, a reporting process is active in the system server 14 to formulate a migraine prediction metric for an individual. The migraine prediction metric is transmitted from the system server 14 to a mobile device 12 that is associated with the individual.

A communication process is active within the mobile device 12 to receive communications, including migraine prediction metrics, from the system server 14. Upon receipt of a migraine prediction metric, the mobile device 12 initiates a process that selects a subset of the sensor signals and the reported migraine event record data that are associated with a particular individual. The process then applies the received migraine prediction metric to the combined sensor signals and reported migraine event record data to create a migraine prediction for the particular individual. In an alternative embodiment, the migraine prediction metric may be applied to the sensor signals associated with a particular individual to create a migraine prediction score for the particular individual.

The process in the mobile device then evaluates the created migraine prediction score against a pre-determined score value, where the score value represents the likelihood of a particular individual experiencing a migraine in the near future. If the migraine prediction score for the individual exceeds the pre-determined score value, the particular individual is likely to experience a migraine within a short time frame. If the migraine prediction score for the individual does not exceed the pre-determined score value, the particular individual is not expected to experience a migraine within a short time frame. When the individual is expected to experience a migraine because the migraine prediction score exceeds the pre-determined score value, a migraine alert message is formulated along with a recommendation for preventing, delaying, or otherwise preparing for a migraine episode and displayed to the particular individual on the display screen of the mobile device. The migraine prediction alert message and recommendation are transmitted by the system server to any mobile device associated with the user to permit the user to take action according to the recommendation to prevent and/or reduce the severity of a migraine episode. Thus, the particular individual associated with the mobile device is alerted to an incipient migraine event to permit the particular individual to take action to change behavior or perform other prophylactic measures to keep the migraine headache from occurring, or keep the severity of the migraine episode to as low a pain level experience as the recommended migraine prophylactic measures will allow.

Figure 5:
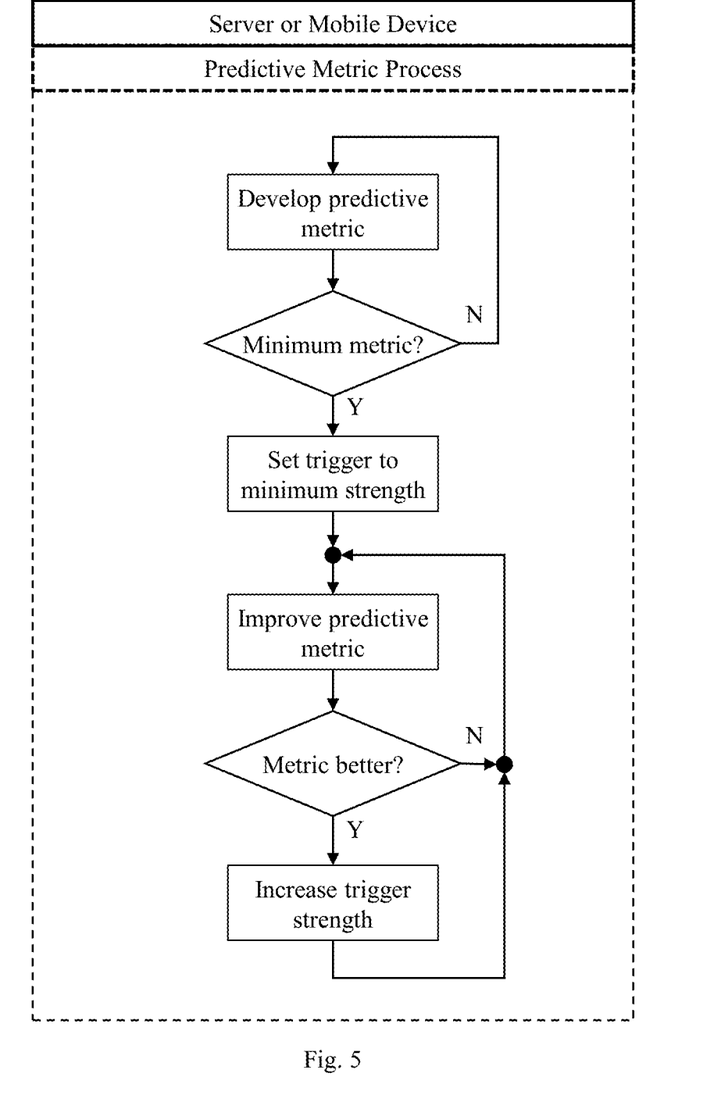
FIG. 5 is an operational flow diagram for flow for the creation and optimization of a predictive metric regarding incipient migraine possibilities for transmission to an individual consistent with certain embodiments of the present invention.

Turning now to FIG. 5, this figure presents an operational flow diagram for flow for the creation and optimization of a predictive metric regarding incipient migraine possibilities for transmission to an individual consistent with certain embodiments of the present invention. In this embodiment, updating a prediction metric to optimize the ability of the metric to provide migraine inception recommendations may occur in a system server 14 or as a process within a mobile device 12 associated with a particular user.

In an embodiment, the Predictive Metric Process, suitable for implementation in a system server 14 or as a process within a mobile device 12 associated with a particular user, initially to identify each of a plurality of possible trigger(s), $T_N$, of a particular user, and, thereafter, to become increasingly sensitive to each identified trigger. To enable this process, the memory in the Server 14 (or Mobile Device 12) is adapted, for each individual, to store N trigger strength indicators, $S_N$, each corresponding to a respective one of the $T_N$ triggers. The process is active to collect and periodically analyze, using known regression analysis techniques, the user's event records and associated environmental sensor signals to develop a predictive metric for each possible trigger. The predictive metric is analyzed in coordination with the combined sensor signals and reported migraine event record data for each individual to create one or more triggers and/or trigger strength indicators to formulate the migraine prediction message and the recommended course of action to prevent and/or reduce the severity of a migraine episode for the particular individual.

Once the metric of a particular trigger, e.g., Tx, exceeds a selected minimum threshold, the system sets a respective one of the trigger strength indicators, Sx, to a predetermined minimum value to indicate that potential trigger Tx might, in time, prove to be a trigger in fact. Thereafter, as additional events (with associated sensor signals) are recorded, the system may continue to improve the predictive metric. When the system detects a strengthening of the prediction metric for a trigger Tx, the process is active to increase the respective trigger strength indicator Sx. Once the strength of trigger strength indicator Sx has surpassed a predetermined significance threshold, the trigger Tx is considered as having been proven, and, thereafter, the system may cast predictions with respect to trigger Tx.

In an embodiment, the system may continue to recursively refine the developed predictive metric for trigger $T_N$ until the respective strength indictor $S_N$ attains a maximum strength value. In a non-limiting example, the predictive metric process represents an adaptive alternative to the binary approach discussed above, where the metric was considered to be either significant or not, based on purely probabilistic criteria. In an embodiment, each trigger may likely require care in the selection of the several thresholds that are used in the analysis of whether the strength of the prediction metric is acceptable, in the calibration of the strength indicators and with respect to the parameters related to the decision points in the flow.

Figure 6:
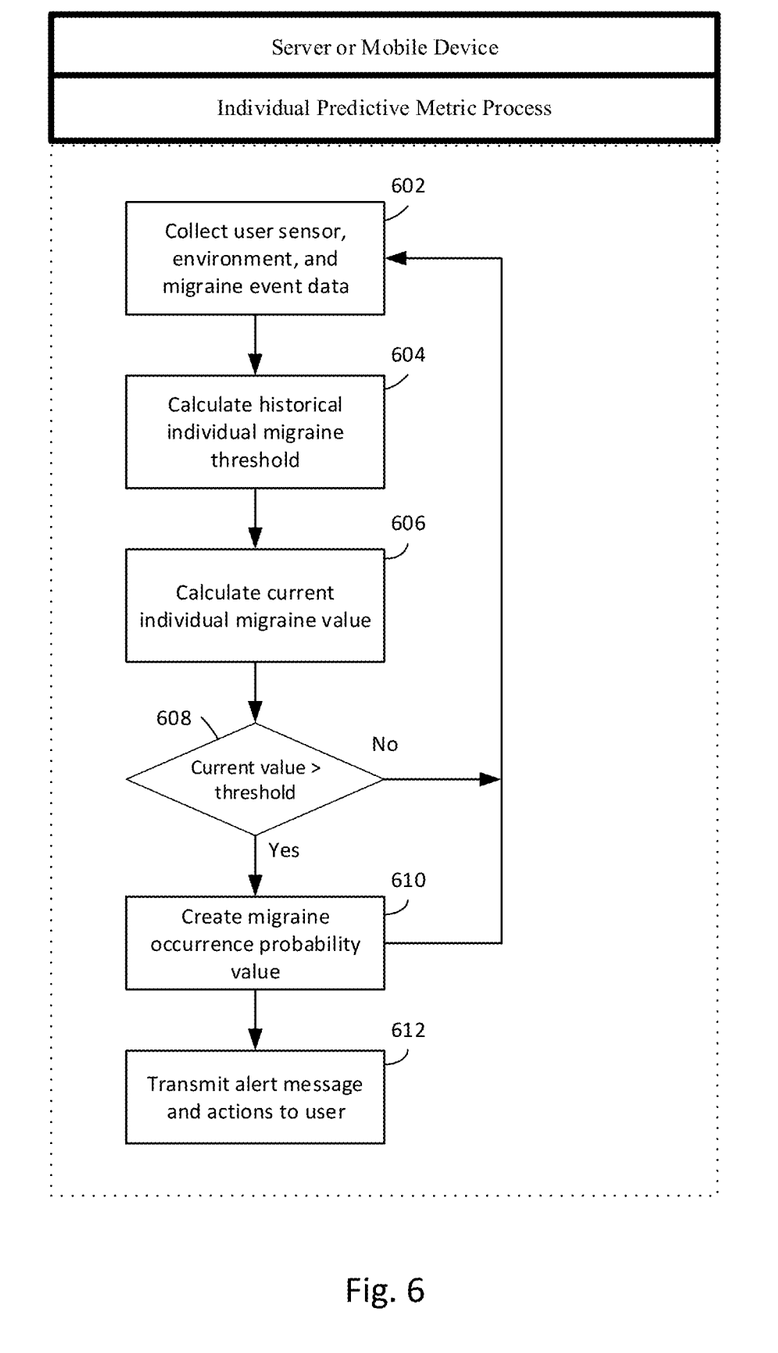
FIG. 6 is a view of the process flow for the creation of an individualized alert for transmission to a selected individual consistent with certain embodiments of the present invention.

Turning now to FIG. 6, this figure presents a view of the process flow for the creation of an individualized alert for transmission to a selected individual consistent with certain embodiments of the present invention. In an embodiment, for each individual the system may collect information about a user including sensor data, environmental data, migraine event data, and personal information about the individual at 602. The system is active to calculate an individual migraine threshold value that is based upon the historical record of all information collected for the individual over the time that the system has been in use by the individual user at 604. This historical individual migraine threshold value presents the best threshold marker for indicating when the individual user has actually experienced a migraine. At 606 the system utilizes all sensor, environmental, migraine event, and personal information collected for the most recent time period or reported event and calculate a current individual migraine value. At 608, the current individual migraine value is compared against the historical individual migraine threshold value. If the current individual migraine value does not exceed the historical individual migraine threshold value no further action is required to create or direct recommendation actions to a user and the system returns to collecting data at 602.

If the current individual migraine value exceeds the historical individual migraine threshold value the system may create a migraine probability value at 610 that indicates the likelihood of a migraine event, the severity of the event, and the need for further action to assist the user. At 612 the system may create a migraine alert message, a list of recommended actions, and a predicted time frame in which the migraine will likely occur and transmits this information for display to an individual user on a display device associated with the individual user.

While certain illustrative embodiments have been described, it is evident that many alternatives, modifications, permutations and variations will become apparent to those skilled in the art in light of the foregoing description.

What is claimed is:

1. A system for the prediction of a migraine episode, comprising:
 a server in data communication with said mobile device;
 a data processor configured within a mobile device in data communication with one or more sensors collecting sensor data from said one or more sensors and migraine event data from a user when a user has indicated that a migraine event has occurred;
 the data processor aggregating all sensor data, environmental data, and all migraine event data and transmitting said aggregated data to the server over a data communication channel;
 the server analyzing all aggregated and collected data from said mobile device to create a historical migraine occurrence threshold value for said user;
 the data processor calculating a current migraine occurrence value for said user;
 the data processor comparing said current migraine occurrence value against said historical migraine occurrence threshold value for said user to create a migraine occurrence probability value;
 the server comparing said migraine occurrence probability value against a pre-set migraine occurrence probability value and where said migraine occurrence probability value exceeds said pre-set migraine occurrence threshold value creating a migraine prediction alert message and recommendation;
 the server transmitting the migraine prediction alert message and recommendation to said mobile device to permit the user to take action according to said recommendation to prevent and/or reduce the severity of a migraine episode.

2. The system of claim 1, further comprising said migraine prediction alert message associated with a pre-configured time frame.

3. The system of claim 1, where sensor data is collected from sensors comprising a pressure sensor, light sensor, audio sensor, touch sensor, or any other sensor that may be triggered manually by an individual, or that may be triggered automatically by changes in the environment surrounding the individual.

4. The system of claim 3, where the sensor or sensors are in data communication with a mobile device that is associated with a user.

5. The system of claim 1, where the migraine prediction alert message comprises generating daily and hourly migraine forecasts for each user.

6. The system of claim 1, where the migraine occurrence probability is associated with at least one migraine trigger for an individual user.

7. The system of claim 1, where the migraine occurrence probability is associated with at least one trigger strength indicator for an individual user.

8. The system of claim 1, where the environmental data comprises at least weather data using a patient's recorded location, further comprising at least humidity, barometric pressure, temperature, wind speed readings, pollen counts, air pollution and particulate matter readings, and other environmental conditions at the patient's location and storing these readings in an electronic storage data record.

9. The system of claim 1, where said aggregated data is appended to the existing data in a training/historical dataset to retrain and improve the predictive models and the individual prediction metric values for each individual.

10. The system of claim 1, where collected sensor data, environmental data, and migraine event data input by a user are combined at the system server to create an entry into a migraine diary maintained by the system server and associated with an individual.

* * * * *